(12) United States Patent
Roelant et al.

(10) Patent No.: US 8,916,535 B2
(45) Date of Patent: Dec. 23, 2014

(54) USE OF 2',5'-OLIGOADENYLATE DERIVATIVE COMPOUNDS

(75) Inventors: Christiaan Roelant, Leuven (BE); Kenny De Meirleir, Mechelen (BE)

(73) Assignee: Protea Biopharma N.V., Neder-Over-Heembeek (BE)

( * ) Notice: Subject to any disclaimer, the term of this patent is extended or adjusted under 35 U.S.C. 154(b) by 50 days.

(21) Appl. No.: 13/880,206

(22) PCT Filed: Nov. 10, 2011

(86) PCT No.: PCT/EP2011/069824
§ 371 (c)(1),
(2), (4) Date: Apr. 18, 2013

(87) PCT Pub. No.: WO2012/062847
PCT Pub. Date: May 18, 2012

(65) Prior Publication Data
US 2013/0237492 A1    Sep. 12, 2013

Related U.S. Application Data

(60) Provisional application No. 61/412,002, filed on Nov. 10, 2010.

(30) Foreign Application Priority Data

Nov. 10, 2010 (GB) .................... 1019043.7

(51) Int. Cl.
*A01N 43/04* (2006.01)
*A61K 31/70* (2006.01)
*C07H 19/207* (2006.01)
*A61K 31/7125* (2006.01)
*A61K 31/7076* (2006.01)
*A61K 45/06* (2006.01)
*C07H 21/00* (2006.01)

(52) U.S. Cl.
CPC .......... *C07H 19/207* (2013.01); *A61K 31/7125* (2013.01); *A61K 31/7076* (2013.01); *A61K 45/06* (2013.01); *C07H 21/00* (2013.01)
USPC ..................... 514/47; 514/43; 514/45; 514/46

(58) Field of Classification Search
None
See application file for complete search history.

(56) References Cited

FOREIGN PATENT DOCUMENTS

WO    WO 93/17692 A1    9/1993

OTHER PUBLICATIONS

International Search Report for International Application No. PCT/EP2011/069824, mailed on Jan. 23, 2012.
Pauwels et al., "Biological Activity of New 2-5A Analogues," *Chemica Scripta*, vol. 26, pp. 141-145 (1986).

*Primary Examiner* — Patrick Lewis
(74) *Attorney, Agent, or Firm* — Knobbe, Martens, Olson & Bear LLP

(57) ABSTRACT

The invention relates to the therapeutic uses of 2',5'-oligoadenylate derivative compounds, more particularly for the treatment of chronic fatigue syndrome (CFS) and in the treatment of infection by a gamma-retrovirus.

15 Claims, No Drawings

USE OF 2',5'-OLIGOADENYLATE DERIVATIVE COMPOUNDS

CROSS-REFERENCE TO RELATED APPLICATIONS

This application is the U.S. National Phase under 35 U.S.C. §371 of International Application PCT/EP2011/069824, filed Nov. 10, 2011, which claims priority to U.S. Provisional Application No. 61/412,002, filed Nov. 10, 2010 and GB 1019043.7, filed Nov. 10, 2010.

FIELD OF THE INVENTION

The present invention relates to certain therapeutic uses of 2',5'-oligoadenylate derivative compounds. In particular, the invention relates to the therapeutic use of 2',5'-oligoadenylate derivative compounds in the treatment of chronic fatigue syndrome (CFS) and in the treatment of infection by a gamma-retrovirus.

BACKGROUND OF THE INVENTION

Chronic fatigue syndrome is a difficult to diagnose, ubiquitous disorder characterized by extreme fatigue, lymph gland enlargement and constitutional symptoms such as weight loss, loss of appetite, memory deterioration and loss of intelligence in some patients. Some CFS patients manifest neuropsychiatric changes such as depression, loss of memory and similar derangements. Thus, chronic fatigue syndrome is sometimes difficult to distinguish from entirely neurological disorders, particularly situational depression. An accumulating body of evidence suggests that CFS is associated with disregulation of both humoral and cellular immunity, including mitogen response, reactivation of viruses, abnormal cytokine production, diminished natural killer cell function and changes in intermediary metabolites. It has been suggested that the clinical and immunological abnormalities observed in CFS might include defects in the double-stranded RNA (dsRNA)-dependent, interferon-inducible pathways, the 2',5'-oligoadenylate (2-5A) synthetase/RNase L and p68 kinase (PKR) antiviral defense pathways (Suhadolnik et al., *Clin. Infect. Dis.* 18: S96-S104, 1994; Suhadolnik et al., *In Vivo* 8: 599-604, 1994).

Gamma-retroviruses are a genus of the retroviridae family. A retrovirus is an RNA virus that is replicated in a host cell via the enzyme reverse transcriptase to produce DNA from its RNA genome. The DNA is then incorporated into the host's genome by an integrase enzyme. The virus thereafter replicates as part of the host cell's DNA. Gamma-retroviruses include amongst others the murine leukemia virus (MLV) that causes cancer in murine hosts and may infect other vertebrates and the feline leukemia virus (FeLV) that infects cats. Xenotropic murine leukemia virus-related virus (XMRV) is an infectious human gamma-retrovirus. Recently, it has been suggested that XMRV may be a contributing factor in the pathogenesis of CFS. Studying peripheral blood mononuclear cells from CFS patients, DNA from XMRV was identified in 67% of patients as compared with 3.7% of healthy controls (Lombardi et al., *Science* 23; 326(5952): 585-9, 2009). Furthermore, MLV-related virus gene sequences were found in 86.5% of patients meeting accepted diagnostic criteria for CFS compared with 6.8% of healthy blood donors (Shyh-Ching et al., *PNAS* 107; 36: 15874-79, 2010). It is noted however that these results were not reproduced by successive studies. XMRV or MLV sequences were not amplified from DNA originating from CFS patients in the UK (Erlwein et al., *PLoS One* 5(1): e8519, 2010). Moreover, no evidence of infection with XMRV was found in a US study population of CFS patients or healthy controls by using multiple molecular and serologic assays (Switzer et al., *Retrovirology* 7(1): 57, 2010). In addition, no association between XMRV infection and CFS was observed in samples from CFS patients from two UK cohorts and from controls tested, either by PCR or serological methodologies (Groom et al., *Retrovirology* 7: 10, 2010). Therefore, the role of XMRV in the pathogenesis of CFS remains to be clarified.

The 2-5A synthetase/RNase L pathway is part of the antiviral defense mechanism in mammalian cells. During viral infection, 2-5A synthetase is activated by dsRNA, derived from viral replicative intermediates. Activated 2-5A synthetase converts ATP to 2',5'-linked oligoadenylates. Biologically active 2-5A binds to and activates a latent endoribonuclease, RNase L, leading to its dimerization and activation. Activated RNase L hydrolyzes single-stranded viral and cellular RNA, thereby inhibiting protein synthesis.

Many viruses have evolved mechanisms to down-regulate or circumvent the antiviral pathways. For example, it has been found that in patients infected with HIV-1, the 2-5A synthetase/RNase L antiviral defense pathway is down-regulated. RNase L is inactivated in HIV-1 infected cells by the overexpression of a naturally occurring RNase L inhibitor, which blocks the binding of 2-5A to RNase L, thereby preventing RNase L activation. It has been shown that a synthetic 2-5A agonist activates RNase L and inhibits the synthesis of viral RNA and the production of infectious HIV-1 particles. Accordingly, the antiviral effect of synthetic 2',5'-oligoadelylate compounds is considered to be based on a counteraction of the down-regulated 2-5A synthetase/RNase L pathways by activation of RNase L (Dimitrova et al., *AIDS Res Hum Retroviruses* 23(1): 123-134, 2007).

Various 2',5'-oligoadenylate derivative compounds have been described with antiviral effects. EP 0 630 249 describes a broad range of 2',5'-oligoadenylate derivative compounds and their use for the inhibition of viral infection in a mammal. The compounds are described to activate the intracellular latent RNase L and also inhibit the action of viral DNA polymerases. WO98/56385 describes base-modified derivatives of 2',5'-oligoadenylate and antiviral uses thereof. WO89/12380 relates to the therapeutic uses of 2',5'-oligoadenylate derivatives in the treatment of chronic infection with viruses including but not limited to human B-lymphotropic virus (HBLV).

U.S. Pat. No. 4,464,359 describes 2',5'-oligoadenylates and derivatives thereof as an antiviral material effective against Herpes simplex infection and effective in inhibiting the transformation of cells infected with Epstein Barr virus. U.S. Pat. No. 4,924,624 relates to 2',5'-phosphorothioate oligoadenylates and a method of inhibiting viral infection in plants. U.S. Pat. No. 4,981,957 relates to oligonucleotides with modified phosphate and modified carbohydrate moieties at the respective chain termini and to their biological uses as mediators of the action of interferon and as antiviral agents.

It has been reported that in chronic fatigue syndrome patients, the 2-5A synthetase/RNase L pathway appears to be up-regulated with increased levels of bioactive 2-5A synthetase, elevated bioactive 2-5A levels and increased activity of the RNase L enzyme (Suhadolnik et al., *Clin. Infect. Dis.* 18: S96-S104, 1994; Suhadolnik et al., *In Vivo* 8: 599-604, 1994; Nijs and De Meirleir In Vivo 19(6): 1013-21, 2005).

There remains a need for compounds for use in the treatment of CFS and in the treatment of infection by a gamma-retrovirus.

SUMMARY OF THE INVENTION

The present invention relates to the use of 2',5'-oligoadenylate derivative compounds in the treatment of chronic fatigue syndrome and in the treatment of infection by a gamma-retrovirus.

Specifically, the invention comprises compounds of Formula (I), or stereochemically isomeric forms thereof, for use in the treatment of chronic fatigue syndrome and/or in the treatment of infection by a gamma-retrovirus,

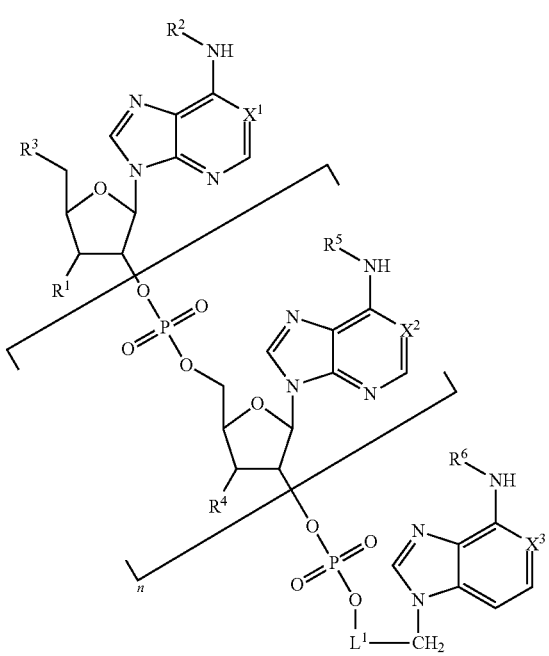

(I)

wherein
n is an integer selected from 1 to 8;
$R^1$ is selected from the group comprising hydrogen, hydroxyl, amino, $-OSi(CH_3)_2C(CH_3)_3$, $C_{1-6}$alkyl, $C_{1-6}$alkylcarbonyloxy and $C_{1-6}$alkoxy;
$R^2$ is selected from the group comprising hydrogen, $C_{1-6}$alkyl, $C_{6-12}$aryl and $C_{6-12}$aryl$C_{1-6}$alkyl;
each $R^4$ is independently selected from the group comprising hydrogen, hydroxyl, amino, $-OSi(CH_3)_2C(CH_3)_3$, $C_{1-6}$alkyl, $C_{1-6}$alkylcarbonyloxy and $C_{1-6}$alkoxy;
each $R^5$ is independently selected from the group comprising hydrogen, $C_{1-6}$alkyl, $C_{6-12}$aryl and $C_{6-12}$aryl$C_{1-6}$alkyl;
$R^6$ is selected from the group comprising hydrogen, $C_{1-6}$alkyl, $C_{6-12}$aryl and $C_{6-12}$aryl$C_{1-6}$alkyl;
$R^3$ is selected from the group comprising hydroxyl,

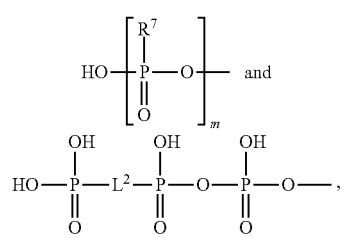

wherein
m is an integer selected from 1, 2 or 3; each $R^7$ is independently selected from the group comprising OH, SH, $C_{1-6}$alkyl and $C_{1-6}$alkoxy; and $L^2$ is selected from $-NH-$ or methylene;
$L^1$ is selected from $C_{1-6}$alkylene or $C_{1-6}$alkyleneoxy;
$X^1$ is selected from N or $^+NR^8$, wherein $R^8$ is selected from the group comprising $C_{1-6}$alkyl, $C_{6-12}$aryl and $C_{6-12}$aryl$C_{1-6}$alkyl;
each $X^2$ is independently selected from N or $^+NR^8$, wherein $R^8$ is selected from the group comprising $C_{1-6}$alkyl, $C_{6-12}$aryl and $C_{6-12}$aryl$C_{1-6}$alkyl;
$X^3$ is selected from N or $^+NR^8$, wherein $R^8$ is selected from the group comprising $C_{1-6}$alkyl, $C_{6-12}$aryl and $C_{6-12}$aryl$C_{1-6}$alkyl; and
wherein at least one of $R^2$, $R^5$, $R^6$ or $R^8$ is selected from $C_{6-12}$aryl or $C_{6-12}$aryl$C_{1-6}$alkyl;
or, a pharmaceutically acceptable salt thereof.

In particular embodiments, the present invention relates to compounds of Formula (I), or stereochemically isomeric forms thereof, for use in the treatment of patients diagnosed with chronic fatigue syndrome and/or for use in the treatment of patients diagnosed with infection by a gamma-retrovirus.

Structural modification of 2-5A compounds provides 2-5A derivative compounds with remarkably increased metabolic stability, while maintaining the ability to activate RNase L. The longer-lasting pharmacological activity of the 2-5A derivative compounds offers a more favorable therapeutic ratio. This allows a decreased frequency of administration relative to authentic 2-5A, which is metabolically unstable. Decreased frequency of administration is important due to the chronic nature of CFS and infections caused by gamma-retroviruses.

In particular embodiments, the invention relates to compounds of Formula (I) as described above, having Formula (II), or stereochemically isomeric forms thereof,

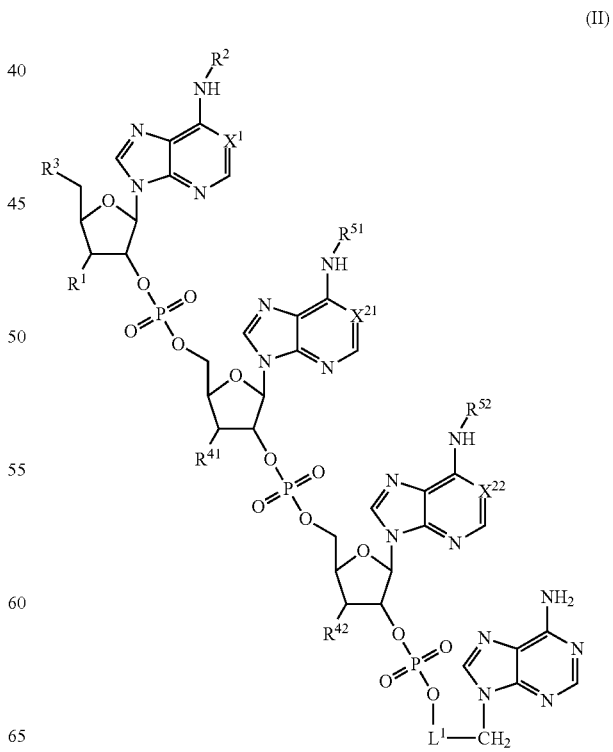

(II)

wherein $R^1, R^2, R^3, X^1$ and $L^1$ have the same meaning as that defined above;

$R^{41}$ is selected from the group comprising hydrogen, hydroxyl, amino, —OSi(CH$_3$)$_2$C(CH$_3$)$_3$, C$_{1-6}$alkyl, C$_{1-6}$alkylcarbonyloxy and C$_{1-6}$alkoxy;

$R^{42}$ is selected from the group comprising hydrogen, hydroxyl, amino, —OSi(CH$_3$)$_2$C(CH$_3$)$_3$, C$_{1-6}$alkyl, C$_{1-6}$alkylcarbonyloxy and C$_{1-6}$alkoxy;

$R^{51}$ is selected from the group comprising hydrogen, C$_{1-6}$alkyl, C$_{6-12}$aryl and C$_{6-12}$arylC$_{1-6}$alkyl;

$R^{52}$ is selected from the group comprising hydrogen, C$_{1-6}$alkyl, C$_{6-12}$aryl and C$_{6-12}$arylC$_{1-6}$alkyl;

$X^{21}$ is selected from N or $^+$NR$^8$, wherein R$^8$ is selected from the group comprising C$_{1-6}$alkyl, C$_{6-12}$aryl and C$_{6-12}$arylC$_{1-6}$alkyl;

$X^{22}$ is selected from N or $^+$NR$^8$, wherein R$^8$ is selected from the group comprising C$_{1-6}$alkyl, C$_{6-12}$aryl and C$_{6-12}$arylC$_{1-6}$alkyl; and wherein at least one of $R^2$, $R^{51}$, $R^{52}$ or $R^8$ is selected from C$_{6-12}$aryl or C$_{6-12}$arylC$_{1-6}$alkyl;

or, a pharmaceutically acceptable salt thereof.

In particular embodiments, the invention relates to compounds of Formula (II) as described above, having Formula (III), or stereochemically isomeric forms thereof, (III)

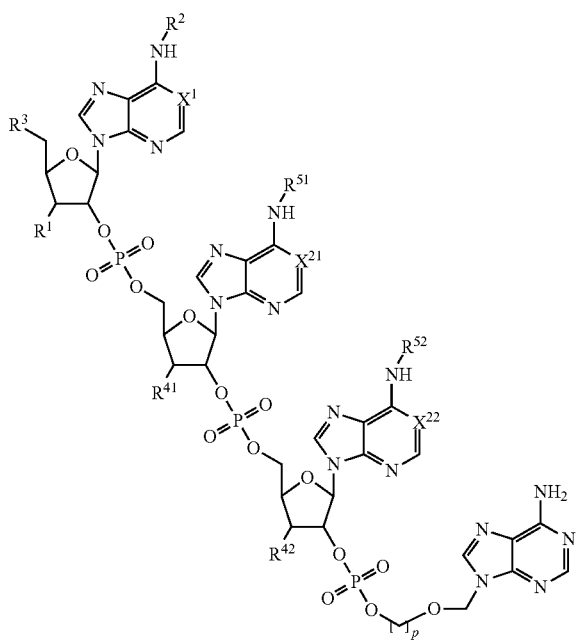

wherein p is an integer selected from 1, 2, 3 or 4;

$R^2, R^3, R^{51}, R^{52}, X^1, X^{21}$ and $X^{22}$ have the same meaning as that defined above.

In particular embodiments, the invention relates to compounds of Formula (II) or (III) as described above, having Formula (IV), or stereochemically isomeric forms thereof, (IV)

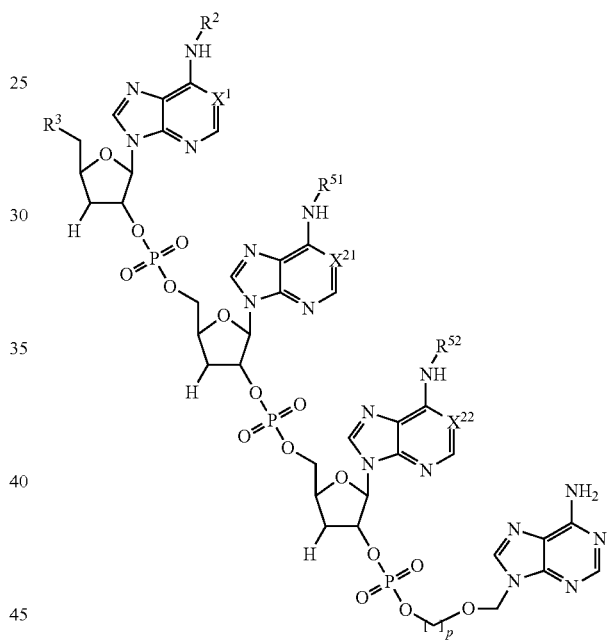

wherein p is an integer selected from 1, 2, 3, 4, 5 or 6;

$R^1, R^2, R^3, R^{41}, R^{42}, R^{51}, R^{52}, X^1, X^{21}$ and $X^{22}$ have the same meaning as that defined above.

In particular embodiments, the invention relates to compounds of Formula (II), (III) or (IV) as described above, having Formula (V), or stereochemically isomeric forms thereof, (V)

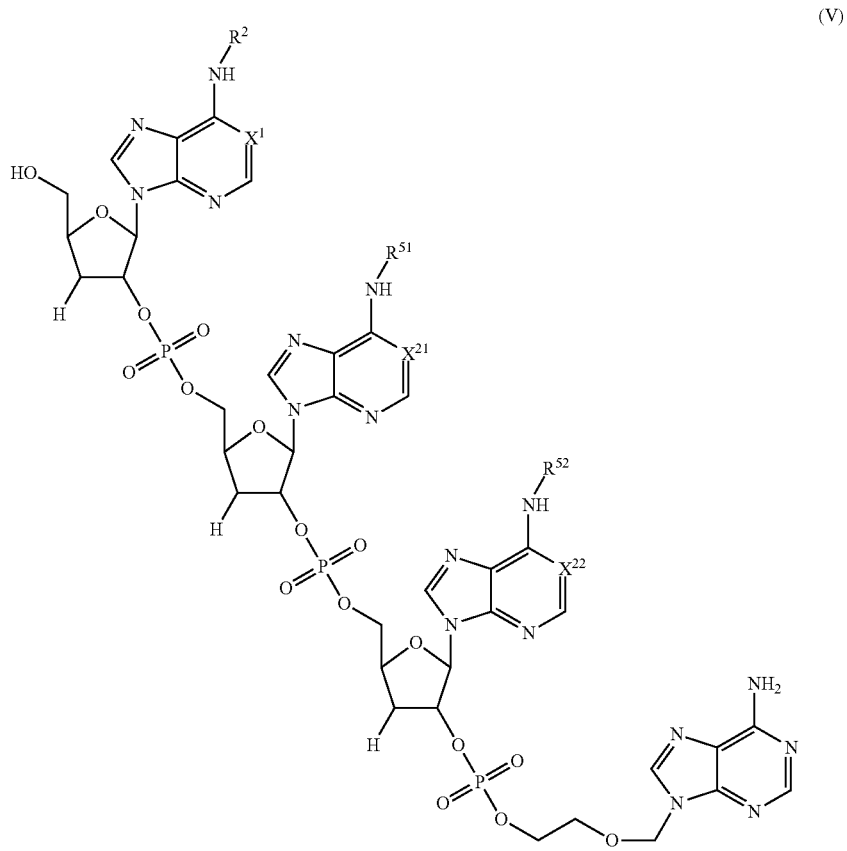

wherein $R^2$, $R^{51}$, $R^{52}$, $X^1$, $X^{21}$ and $X^{22}$ have the same meaning as that defined above.

In particular embodiments, the invention provides compounds of Formula (II), (III), (IV) or (V) as described above, wherein only one of $R^2$, $R^{51}$, $R^{52}$ or $R^8$ is selected from $C_{6-12}$aryl or $C_{6-12}$aryl$C_{1-6}$alkyl.

In particular embodiments, the invention relates to compounds of Formula (II), (III), (IV) or (V) as described above, wherein $R^2$, $R^{51}$ and $R^{52}$ are independently selected from hydrogen or benzyl and only one of $R^2$, $R^{51}$ or $R^{52}$ is benzyl, and $X^1$, $X^{21}$ and $X^{22}$ are N.

In particular embodiments, the invention provides compounds of Formula (II), (III), (IV) or (V) as described above, wherein $R^2$, $R^{51}$ and $R^{52}$ are hydrogen, and $X^1$, $X^{21}$ and $X^{22}$ are independently selected from N or $^+NR^8$, wherein $R^8$ is benzyl and only one of $X^1$, $X^{21}$ or $X^{22}$ is $NR^8$.

In a particular embodiment, the invention relates to a compound of Formula (I), (II), (III), (IV) or (V) as described above, having Formula (VI), or stereochemically isomeric forms thereof.

(VI)
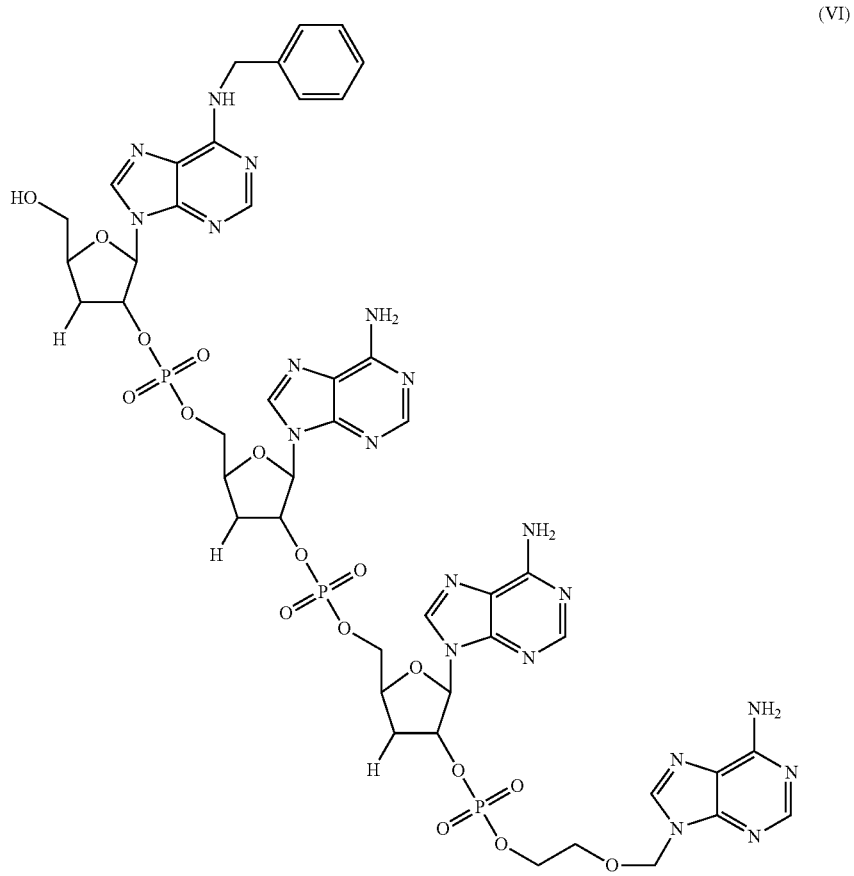
In a particular embodiment, the invention relates to a compound of Formula (I), (II), (III), (IV) or (V) as described above, having Formula (VII), or stereochemically isomeric forms thereof.
(VII)
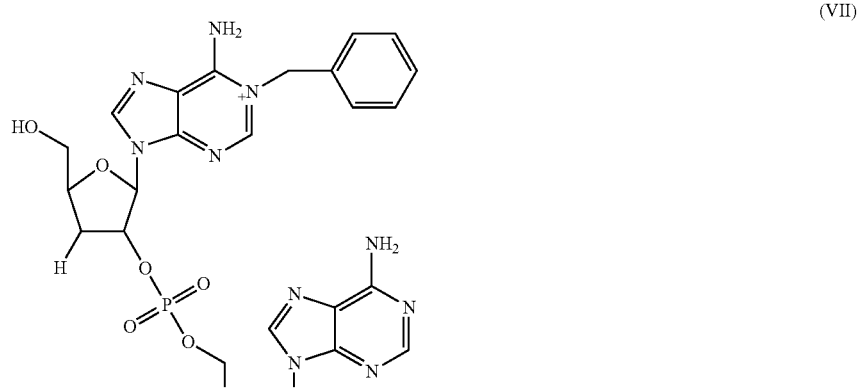

-continued

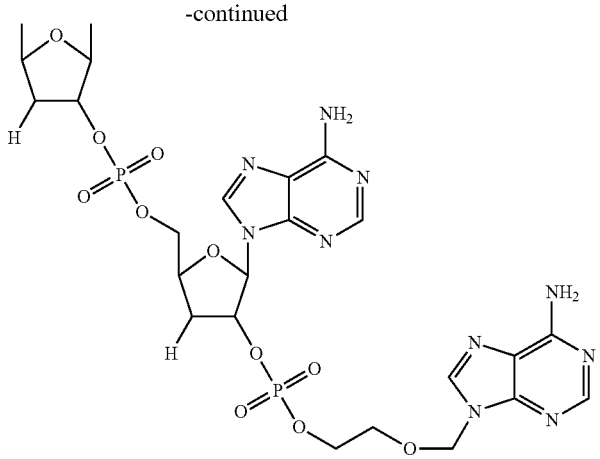

In a particular embodiment, the invention relates to a compound of Formula (I), (II), (III), (IV) or (V) as described above, having Formula (VIII), or stereochemically isomeric forms thereof.

(VIII)

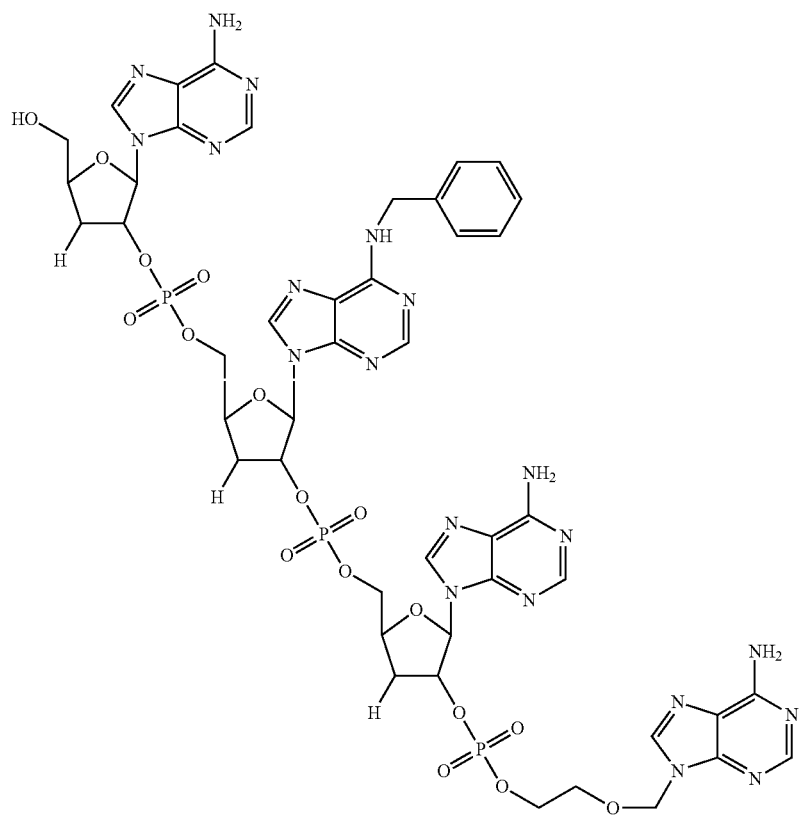

Another aspect of the invention relates to the therapeutic use of the compounds as described above, wherein said compounds are used in combination with at least one other pharmacologically active compound, preferably a viral inhibitor.

In particular embodiments, the invention relates to compounds as described above, wherein said at least one other pharmacologically active compound is selected form the group comprising azidothymidine (AZT), raltegravir, tenofovir, tenofovir disoproxil fumarate (TDF), didanosine, lamivudine, staduvine, abacavir, foscarnet, amantadine, kutapressin, hepapressin, isoprinosine, Gc protein-derived macrophage activating factor (GcMAF), ampligen/poly I:poly C12U, minocycline, doxycycline, azithromycin and the cytidine deaminases APOBEC3F and APOBEC3G.

In further embodiments, the invention relates to compounds as described above, wherein said compounds are used in a pharmaceutical composition comprising a pharmaceutically acceptable excipient and a therapeutically effective amount of at least one compound of Formula (I).

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

DETAILED DESCRIPTION OF THE INVENTION

In the context of the present invention, the terms used are to be construed in accordance with the following definitions, unless a context dictates otherwise.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The present invention relates to the use of 2',5'-oligoadenylate derivative compounds, preferably of Formula (I), in the treatment of chronic fatigue syndrome and/or in the treatment of infection by a gamma-retrovirus.

The term "chronic fatigue syndrome" or "CFS" as referred to herein designates a condition which is diagnosed based on the following criteria (as developed by the U.S. Centers for Disease Control and Prevention in 1994):
1. Clinically evaluated, unexplained persistent or relapsing chronic fatigue that is of new or definite onset (i.e., not lifelong), is not the result of ongoing exertion, is not substantially alleviated by rest, and results in substantial reduction in previous levels of occupational, educational, social, or personal activities.
2. The concurrent occurrence of four or more of the following symptoms: substantial impairment in short-term memory or concentration; sore throat; tender lymph nodes; muscle pain; multi-joint pain without swelling or redness; headaches of a new type, pattern, or severity; unrefreshing sleep; and post-exertional malaise lasting more than 24 hours. These symptoms must have persisted or recurred during 6 or more consecutive months of illness and must not have predated the fatigue.

The present invention relates to compounds for use in the treatment of infection by a gamma-retrovirus and to methods of treatment of infection by gamma-retroviruses which involve the administration of such compounds to a patient. Gamma-retroviruses are a genus of the family of the Retroviridae. Gamma retroviruses include a number of animal viruses such as feline leukemia virus, gibbon ape leukemia virus, guinea pig type-C oncovirus, porcine type-C oncovirus, murine leukemia virus of the mammalian virus group, Finkel-Biskis-Jinkins murine sarcoma virus, Gardner-Arnstein feline sarcoma virus, Hardy-Zuckerman feline sarcoma virus, Harvey murine sarcoma virus, Kirsten murine sarcoma virus, Moloney murine sarcoma virus, Snyder-Theilen feline sarcoma virus, Woolly monkey sarcoma virus of the replication defective viruses, Viper retrovirus of the reptilian virus group, chick syncytial virus, reticuloendotheliosis virus, Trager duck spleen necrosis virus of the avian (reticuloendotheliosis) virus group. Accordingly, the compounds of the present invention are envisaged for veterinary use, more particularly for use in the treatment of non-human animals infected by one or more gamma retroviruses.

The gamma-retroviruses also include a limited number of viruses which are known to infect humans, such as xenotropic murine leukemia virus-related virus (XMRV) and the highly related (polytropic) murine leukemia virus (MLV).

A xenotropic murine leukemia virus-related virus or "XMRV" is an infectious gamma-retrovirus. It was first identified in prostate tumors, particularly in prostate tumors of patients homozygous for RNASEL variant, R462Q (e.g., Urisman et al., PLoS Pathog. 2(3): e25, 2006; Dong et al., Proc. Natl. Acad. Sci. USA 104(5): 655, 2007 and WO 2006/110589). Exemplary strains include strains such as XMRV VP35 (GenBank Accession No. DQ241301), XMRV VP42 (GenBank Accession No. DQ241302) and XMRV VP62 (GenBank Accession No. DQ399707). Methods for the detection of XMRV nucleic acid by polymerase chain reaction (PCR) analysis in samples of patients and normal individuals have been described in WO 2010/075414.

Polytropic murine leukemia viruses share between 87 and 93% nucleotide identity across the genome with XMRV and also have 88-97% and 88-91% amino acid identity to XMRV Gag and Env proteins, respectively.

It has been suggested that gamma-retroviruses, in particular XMRV may be a contributing factor in the pathogenesis of CFS. Accordingly, a subgroup of patients with CFS may be infected with gamma-retroviruses, in particular with XMRV and/or MLV, but not all patients with CFS are necessarily infected with gamma-retroviruses, or in particular with XMRV. Furthermore, not all patients infected with a gamma-retrovirus, or in particular with XMRV or MLV have CFS, but part of the patients infected with a gamma-retrovirus, or in particular with XMRV or MLV may show symptoms of CFS. In an embodiment, the present invention relates to the treatment of patients with CFS in which an infection with a gamma-retrovirus has been identified. In a further embodiment, the present invention relates to the treatment of patients with CFS in which an infection with XMRV and/or (P)MLV has been identified.

The present invention relates to 2',5'-oligoadenylate derivative compounds, preferably of Formula (I), for use in the treatment of, or, in the manufacture of a medicament for the treatment of CFS and/or infection by a gamma-retrovirus. This invention also relates to the use of 2',5'-oligoadenylate derivative compounds in the treatment of, or, in the manufacture of a medicament for the treatment of CFS and/or infection by a gamma-retrovirus.

In an embodiment, the present invention relates to compounds of Formula (I), or stereochemically isomeric forms thereof, for use in the treatment of chronic fatigue syndrome and/or in the treatment of infection by a gamma-retrovirus, wherein n is an integer selected from 1 to 8; for example n is 1, 2, 3, 4, 5, 6, 7 or 8;

$R^1$ is selected from the group comprising hydrogen, hydroxyl, amino, —OSi(CH$_3$)$_2$C(CH$_3$)$_3$, C$_{1-6}$alkyl, C$_{1-6}$alkylcarbonyloxy and C$_{1-6}$alkoxy; preferably $R^1$ is selected from the group comprising hydrogen, hydroxyl, C$_{1-6}$alkyl, C$_{1-6}$alkylcarbonyloxy and $C_{1-6}$alkoxy; preferably $R^1$ is selected from the group comprising hydrogen, hydroxyl and $C_{1-6}$alkyl; preferably $R^1$ is selected from the group comprising hydrogen, hydroxyl and $C_{1-4}$alkyl; preferably $R^1$ is selected from hydrogen or hydroxyl; preferably $R^1$ is hydrogen;

$R^2$ is selected from the group comprising hydrogen, $C_{1-6}$alkyl, $C_{6-12}$aryl and $C_{6-12}$aryl$C_{1-6}$alkyl; preferably $R^2$ is selected from the group comprising hydrogen, $C_{6-12}$aryl and $C_{6-12}$aryl$C_{1-6}$alkyl; preferably $R^2$ is selected from the group comprising hydrogen, $C_6$aryl and $C_6$aryl$C_{1-4}$alkyl; for example $R^2$ is selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; More particularly $R^2$ is selected from the group comprising hydrogen, phenyl, benzyl, phenethyl, methylphenylmethyl, 1-methyl-1-phenyl-ethyl and 1-phenyl-ethyl; Most particularly $R^2$ is selected from hydrogen or benzyl;

each $R^4$ is independently selected from the group comprising hydrogen, hydroxyl, amino, —OSi($CH_3$)$_2$C($CH_3$)$_3$, $C_{1-6}$alkyl, $C_{1-6}$alkylcarbonyloxy and $C_{1-6}$alkoxy; preferably each $R^4$ is independently selected from the group comprising hydrogen, hydroxyl, $C_{1-6}$alkyl, $C_{1-6}$alkylcarbonyloxy and $C_{1-6}$alkoxy; preferably each $R^4$ is independently selected from the group comprising hydrogen, hydroxyl and $C_{1-6}$alkyl; preferably each $R^4$ is independently selected from the group comprising hydrogen, hydroxyl and $C_{1-4}$alkyl; more particularly each $R^4$ is independently selected from hydrogen or hydroxyl; preferably each $R^4$ is hydrogen;

each $R^5$ is independently selected from the group comprising hydrogen, $C_{1-6}$alkyl, $C_{6-12}$aryl and $C_{6-12}$aryl$C_{1-6}$alkyl; preferably each $R^5$ is independently selected from the group comprising hydrogen, $C_{6-12}$aryl and $C_{6-12}$aryl$C_{1-6}$alkyl; preferably each $R^5$ is independently selected from the group comprising hydrogen, $C_6$aryl and $C_6$aryl$C_{1-4}$alkyl; for example each $R^5$ is independently selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably each $R^5$ is independently selected from the group comprising hydrogen, phenyl, benzyl, phenethyl, methylphenylmethyl, 1-methyl-1-phenyl-ethyl and 1-phenyl-ethyl; preferably each $R^5$ is independently selected from hydrogen or benzyl;

$R^6$ is selected from the group comprising hydrogen, $C_{1-6}$alkyl, $C_{6-12}$aryl and $C_{6-12}$aryl$C_{1-6}$alkyl; preferably $R^6$ is selected from the group comprising hydrogen, $C_{6-12}$aryl and $C_{6-12}$aryl$C_{1-6}$alkyl; preferably $R^6$ is selected from the group comprising hydrogen, $C_6$aryl and $C_6$aryl$C_{1-4}$alkyl; for example $R^6$ is selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $R^6$ is selected from the group comprising hydrogen, phenyl, benzyl, phenethyl, methylphenylmethyl, 1-methyl-1-phenyl-ethyl and 1-phenyl-ethyl; preferably $R^6$ is selected from hydrogen or benzyl;

$R^3$ is selected from the group comprising hydroxyl,

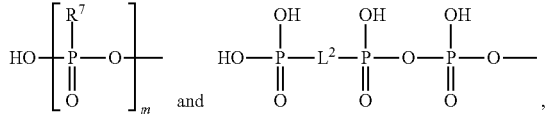

and $m$ is an integer selected from 1, 2 or 3; each $R^7$ is independently selected from the group comprising OH, SH, $C_{1-6}$alkyl and $C_{1-6}$alkoxy, and $L^2$ is selected from —NH— or methylene; preferably $R^3$ is selected from hydroxyl or

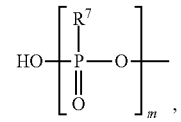

and $m$ is an integer selected from 1, 2 or 3; each $R^7$ is independently selected from the group comprising OH, SH, $C_{1-6}$alkyl and $C_{1-6}$alkoxy; preferably each $R^7$ is independently selected from the group comprising OH, $C_{1-4}$alkyl and $C_{1-4}$alkoxy; preferably each $R^7$ is OH; preferably $R^3$ is hydroxyl.

$L^1$ is selected from $C_{1-6}$alkylene or $C_{1-6}$alkyleneoxy; preferably $L^1$ is $C_{1-6}$alkyleneoxy; preferably $L^1$ is $C_{1-4}$alkyleneoxy; preferably $L^1$ is ethyleneoxy;

$X^1$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^1$ is selected from N or $^+NR^8$, wherein $R^8$ is selected from $C_{6-12}$aryl or $C_{6-12}$aryl$C_{1-6}$alkyl; preferably $X^1$ is selected from N or $^+NR^8$, wherein $R^8$ is selected from $C_6$aryl or $C_6$aryl$C_{1-4}$alkyl; for example $X^1$ is selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $X^1$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^1$ is selected from N or $^+NR^8$, wherein $R^8$ is benzyl;

each $X^2$ is independently selected from N or $^+NR^8$, wherein $R^8$ is selected from the group comprising $C_{1-6}$alkyl, $C_{6-12}$aryl and $C_{6-12}$aryl$C_{1-6}$alkyl; preferably each $X^2$ is independently selected from N or $^+NR^8$, wherein $R^8$ is selected from $C_{6-12}$aryl or $C_{6-12}$aryl$C_{1-6}$alkyl; preferably each $X^2$ is independently selected from N or $^+NR^8$, wherein $R^8$ is selected from $C_6$aryl or $C_6$aryl$C_{1-4}$alkyl; for example each $X^2$ is independently selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably each $X^2$ is independently selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably each $X^2$ is independently selected from N or $^+NR^8$, wherein $R^8$ is benzyl;

$X^3$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^3$ is selected from N or $^+NR^8$, wherein $R^8$ is selected from $C_{6-12}$aryl or $C_{6-12}$aryl$C_{1-6}$alkyl; preferably $X^3$ is selected from N or $^+NR^8$, wherein $R^8$ is selected from $C_6$aryl or $C_6$aryl$C_{1-4}$alkyl; for example $X^3$ is selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $X^3$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^3$ is selected from N or $^+NR^8$, wherein $R^8$ is benzyl; and wherein at least one of $R^2$, $R^5$, $R^6$ or $R^8$ is selected from $C_{6-12}$aryl or $C_{6-12}$aryl$C_{1-6}$alkyl; preferably at least one of $R^2$, $R^5$, $R^6$ or $R^8$ is selected from $C_6$aryl or $C_6$aryl$C_{1-4}$alkyl; for example at least one of $R^2$, $R^5$, $R^6$ or $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably at least one of $R^2$, $R^5$, $R^6$ or $R^8$ is selected from the group comprising phenyl, benzyl, phenethyl, methylphenylmethyl, 1-methyl-1-phenyl-ethyl and 1-phenyl-ethyl; preferably at least one of $R^2$, $R^5$, $R^6$ or $R^8$ is benzyl;

or, a pharmaceutically acceptable salt thereof.

When describing the present compounds, the terms used are to be construed in accordance with the following definitions, unless a context dictates otherwise.

The term "$C_{1-6}$alkyl", as a group or part of a group, refers to a hydrocarbyl radical of Formula $C_nH_{2n+1}$ wherein n is a number ranging from 1 to 6. Generally, alkyl groups of this invention comprise from 1 to 6 carbon atoms, preferably from 1 to 4 carbon atoms, more preferably from 1 to 3 carbon atoms, still more preferably 1 to 2 carbon atoms. Alkyl groups may be linear or branched and may be substituted as indicated herein. When a subscript is used herein following a carbon atom, the subscript refers to the number of carbon atoms that the named group may contain. Thus, for example, $C_{1-6}$alkyl includes all linear, or branched alkyl groups with between 1 and 6 carbon atoms, and thus includes for example methyl, ethyl, n-propyl, i-propyl, 2-methyl-ethyl, butyl and its isomers (e.g. n-butyl, i-butyl and tert-butyl); pentyl and its isomers, hexyl and its isomers, and the like.

The term "$C_{1-6}$alkylcarbonyloxy", as a group or part of a group, represents a group of Formula —O—$COR^a$, wherein $R^a$ is $C_{1-6}$alkyl as defined herein.

The term "$C_{1-6}$alkoxy", as a group or part of a group, refers to a radical having the Formula —$OR^b$ wherein $R^b$ is $C_{1-6}$alkyl as defined herein. Non-limiting examples of suitable alkyloxy include methyloxy, ethyloxy, propyloxy, isopropyloxy, butyloxy, isobutyloxy, sec-butyloxy, tert-butyloxy, pentyloxy and hexyloxy.

The term "$C_{6-12}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 12 atoms; wherein at least one ring is aromatic. Non-limiting examples of $C_{6-12}$aryl comprise phenyl, biphenylyl, biphenylenyl, or 1- or 2-naphthyl.

The term "$C_{6-12}$aryl$C_{1-6}$alkyl", as a group or part of a group, means a $C_{1-6}$alkyl as defined herein, wherein a hydrogen atom is replaced by a $C_{6-12}$aryl as defined herein. Examples of aralkyl radicals include benzyl, phenethyl, dibenzylmethyl, methylphenylmethyl, 1-methyl-1-phenyl-ethyl, 1-phenyl-ethyl, 3-(2-naphthyl)-butyl, and the like.

The term "$C_{1-6}$alkylene", as a group or part of a group, refers to $C_{1-6}$alkyl groups that are divalent, i.e., with two single bonds for attachment to two other groups. Non-limiting examples of alkylene groups includes methylene, ethylene, methylmethylene, propylene, ethylethylene, 1-methylethylene and 1,2-dimethylethylene.

The term "$C_{1-6}$alkyleneoxy", as a group or part of a group, refers to a radical having the Formula —$OR^c$— wherein $R^c$ is $C_{1-6}$alkyl as defined herein. Non-limiting examples of suitable alkyleneoxy include methyleneoxy, ethyleneoxy, propyleneoxy, isopropyleneoxy, butyleneoxy, isobutyleneoxy, sec-butyleneoxy, tert-butyleneoxy, pentyleneoxy and hexyleneoxy.

Whenever used hereinafter, the term "present compounds" or a similar term is meant to include all the compounds of Formula (I), (II), (III), (IV), (V), (VI), (VII) or (VIII). This term also refers to their salts, stereochemically isomeric forms, solvates, hydrates, racemic mixtures, pro-drugs, esters and metabolites.

The terms described above and others used in the specification are well understood to those in the art.

The compounds according to the invention contain one or more asymmetric carbon atoms that serve as chiral center, which may lead to different optical forms (e.g. enantiomers or diastereoisomers). The invention comprises all such optical forms in all possible configurations, as well as mixtures thereof.

More generally, from the above, it will be clear to the skilled person that the present compounds may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds. All such possible isomers, tautomers, and mixtures thereof are included within the scope of the invention.

The term "stereochemically isomeric forms" of the compounds according to the invention, as used herein, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound herein encompasses the mixture of all possible stereochemically isomeric forms, which said compound may possess. Said mixture may contain all diastereomers and/or enantiomers of the basic molecular structure of said compound. All stereochemically isomeric forms of the compounds either in pure form or in admixture with each other are intended to be embraced within the scope of the present invention.

Preferred features of the compounds of this invention are now set forth.

One embodiment of the present invention concerns compounds of the Formula (II), or stereochemically isomeric forms thereof, for use in the treatment of chronic fatigue syndrome and/or in the treatment of infection by a gamma-retrovirus, wherein $R^1$, $R^2$, $R^3$, $X^1$ and $L^1$ have the same meaning as that defined above;

$R^{41}$ is selected from the group comprising hydrogen, hydroxyl, amino, —$OSi(CH_3)_2C(CH_3)_3$, $C_{1-6}$alkyl, $C_{1-6}$alkylcarbonyloxy and $C_{1-6}$alkoxy; preferably $R^{41}$ is selected from the group comprising hydrogen, hydroxyl, $C_{1-6}$alkyl, $C_{1-6}$alkylcarbonyloxy and $C_{1-6}$alkoxy; preferably $R^{41}$ is selected from the group comprising hydrogen, hydroxyl and $C_{1-6}$alkyl; preferably $R^{41}$ is selected from the group comprising hydrogen, hydroxyl and $C_{1-4}$alkyl; preferably $R^{41}$ is selected from hydrogen or hydroxyl; preferably $R^{41}$ is hydrogen;

$R^{42}$ is selected from the group comprising hydrogen, hydroxyl, amino, —$OSi(CH_3)_2C(CH_3)_3$, $C_{1-6}$alkyl, $C_{1-6}$alkylcarbonyloxy and $C_{1-6}$alkoxy; preferably $R^{42}$ is selected from the group comprising hydrogen, hydroxyl, $C_{1-6}$alkyl, $C_{1-6}$alkylcarbonyloxy and $C_{1-6}$alkoxy; preferably $R^{42}$ is selected from the group comprising hydrogen, hydroxyl and $C_{1-6}$alkyl; preferably $R^{42}$ is selected from the group comprising hydrogen, hydroxyl and $C_{1-4}$alkyl; preferably $R^{42}$ is selected from hydrogen or hydroxyl; preferably $R^{42}$ is hydrogen;

$R^{51}$ is selected from the group comprising hydrogen, $C_{1-6}$alkyl, $C_{6-12}$aryl and $C_{6-12}$aryl$C_{1-6}$alkyl; preferably $R^{51}$ is selected from the group comprising hydrogen, $C_{6-12}$aryl and $C_{6-12}$aryl$C_{1-6}$alkyl; preferably $R^{51}$ is selected from the group comprising hydrogen, $C_6$aryl and $C_6$aryl$C_{1-4}$alkyl; for example $R^{51}$ is selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $R^{51}$ is selected from the group comprising hydrogen, phenyl, benzyl, phenethyl, methylphenylmethyl, 1-methyl-1-phenyl-ethyl and 1-phenyl-ethyl; preferably $R^{51}$ is selected from hydrogen or benzyl;

$R^{52}$ is selected from the group comprising hydrogen, $C_{1-6}$alkyl, $C_{6-12}$aryl and $C_{6-12}$aryl$C_{1-6}$alkyl; preferably $R^{52}$ is selected from the group comprising hydrogen, $C_{6-12}$aryl and $C_{6-12}$aryl$C_{1-6}$alkyl; preferably $R^{52}$ is selected from the group comprising hydrogen, $C_6$aryl and $C_6$aryl$C_{1-4}$alkyl; for example $R^{52}$ is selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $R^{52}$ is selected from the group comprising hydrogen, phenyl, benzyl, phenethyl, methylphenylmethyl, 1-methyl-1-phenyl-ethyl and 1-phenyl-ethyl; preferably $R^{52}$ is selected from hydrogen or benzyl;

$X^{21}$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^{21}$ is selected from N or $^+NR^8$, wherein $R^8$ is selected from $C_{6-12}$aryl or $C_{6-12}$aryl$C_{1-6}$alkyl; preferably $X^{21}$ is selected from N or $^+NR^8$, wherein $R^8$ is selected from $C_6$aryl or $C_6$aryl$C_{1-4}$alkyl; for example $X^{21}$ is selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $X^{21}$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^{21}$ is selected from N or $^+NR^8$, wherein $R^8$ is benzyl;

$X^{22}$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^{22}$ is selected from N or $^+NR^8$, wherein $R^8$ is selected from $C_{6-12}$aryl or $C_{6-12}$aryl$C_{1-6}$alkyl; preferably $X^{22}$ is selected from N or $^+NR^8$, wherein $R^8$ is selected from $C_6$aryl or $C_6$aryl$C_{1-4}$alkyl; for example $X^{22}$ is selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably $X^{22}$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^{22}$ is selected from N or $^+NR^8$, wherein $R^8$ is benzyl; and wherein at least one of $R^2$, $R^{51}$, $R^{52}$ or $R^8$ is selected from $C_{6-12}$aryl or $C_{6-12}$aryl$C_{1-6}$alkyl; preferably at least one of $R^2$, $R^{51}$, $R^{52}$ or $R^8$ is selected from $C_6$aryl or $C_6$aryl$C_{1-4}$alkyl; for example at least one of $R^2$, $R^{51}$, $R^{52}$ or $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably at least one of $R^2$, $R^{51}$, $R^{52}$ or $R^8$ is selected from the group comprising phenyl, benzyl, phenethyl, methylphenylmethyl, 1-methyl-1-phenyl-ethyl and 1-phenyl-ethyl; preferably at least one of $R^2$, $R^{51}$, $R^{52}$ or $R^8$ is benzyl;

or, a pharmaceutically acceptable salt thereof.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $R^1$ is selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy; preferably $R^1$ is selected from the group comprising hydrogen, hydroxyl, $C_{1-6}$alkyl, $C_{1-6}$alkylcarbonyloxy and $C_{1-6}$alkoxy; preferably $R^1$ is selected from the group comprising hydrogen, hydroxyl and $C_{1-6}$alkyl; preferably $R^1$ is selected from the group comprising hydrogen, hydroxyl and $C_{1-4}$alkyl; preferably $R^1$ is selected from hydrogen or hydroxyl; preferably $R^1$ is hydrogen.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $R^2$ is selected from the group comprising hydrogen, $C_{1-6}$alkyl, $C_{6-12}$aryl and $C_{6-12}$aryl$C_{1-6}$alkyl; preferably $R^2$ is selected from the group comprising hydrogen, $C_{6-12}$aryl and $C_{6-12}$aryl$C_{1-6}$alkyl; preferably $R^2$ is selected from the group comprising hydrogen, $C_6$aryl and $C_6$aryl$C_{1-4}$alkyl; preferably $R^2$ is selected from the group comprising hydrogen, phenyl, benzyl, phenethyl, methylphenylmethyl, 1-methyl-1-phenyl-ethyl and 1-phenyl-ethyl; preferably $R^2$ is selected from hydrogen or benzyl.

One embodiment of the present invention concerns compounds of the Formula (I), or stereochemically isomeric forms thereof, for use in the treatment of chronic fatigue syndrome and/or in the treatment of infection by a gamma-retrovirus, wherein each $R^4$ is independently selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy; preferably each $R^4$ is independently selected from the group comprising hydrogen, hydroxyl, $C_{1-6}$alkyl, $C_{1-6}$alkylcarbonyloxy and $C_{1-6}$alkoxy; preferably each $R^4$ is independently selected from the group comprising hydrogen, hydroxyl and $C_{1-6}$alkyl; preferably each $R^4$ is independently selected from the group comprising hydrogen, hydroxyl and $C_{1-4}$alkyl; preferably each $R^4$ is independently selected from hydrogen or hydroxyl; preferably each $R^4$ is hydrogen.

One embodiment of the present invention concerns compounds of the Formula (I), or stereochemically isomeric forms thereof, for use in the treatment of chronic fatigue syndrome and/or in the treatment of infection by a gamma-retrovirus, wherein each $R^5$ is independently selected from the group comprising hydrogen, $C_{1-6}$alkyl, $C_{6-12}$aryl and $C_{6-12}$aryl$C_{1-6}$alkyl; preferably each $R^5$ is independently selected from the group comprising hydrogen, $C_{6-12}$aryl and $C_{6-12}$aryl$C_{1-6}$alkyl; preferably each $R^5$ is independently selected from the group comprising hydrogen, $C_6$aryl and $C_6$aryl$C_{1-4}$alkyl; for example each $R^5$ is independently selected from the group comprising hydrogen, phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably each $R^5$ is independently selected from the group comprising hydrogen, phenyl, benzyl, phenethyl, methylphenylmethyl, 1-methyl-1-phenyl-ethyl and 1-phenyl-ethyl; preferably each $R^5$ is independently selected from hydrogen or benzyl.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $R^6$ is selected from the group comprising hydrogen, $C_{1-6}$alkyl, $C_{6-12}$aryl and $C_{6-12}$aryl$C_{1-6}$alkyl; preferably $R^6$ is selected from the group comprising hydrogen, $C_{6-12}$aryl and $C_{6-12}$aryl$C_{1-6}$alkyl; preferably $R^6$ is selected from the group comprising hydrogen, $C_6$aryl and $C_6$aryl$C_{1-4}$alkyl; preferably $R^6$ is selected from the group comprising hydrogen, phenyl, benzyl, phenethyl, methylphenylmethyl, 1-methyl-1-phenyl-ethyl and 1-phenyl-ethyl; preferably $R^6$ is selected from hydrogen or benzyl.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $R^3$ is selected from the group comprising hydroxyl,

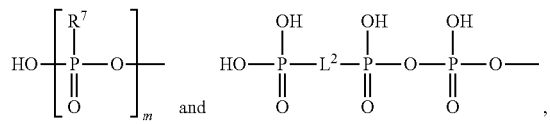

and m is an integer selected from 1, 2 or 3; each $R^7$ is independently selected from the group comprising OH, SH, $C_{1-6}$alkyl and $C_{1-6}$alkoxy, and $L^2$ is selected from —NH— or methylene;

preferably $R^3$ is selected from hydroxyl or

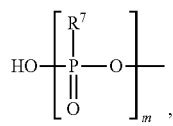

and m is an integer selected from 1, 2 or 3; each $R^7$ is independently selected from the group comprising OH, SH, $C_{1-6}$alkyl and $C_{1-6}$alkoxy; preferably each $R^7$ is independently selected from the group comprising OH, $C_{1-4}$alkyl and $C_{1-4}$alkoxy; preferably each $R^7$ is OH;

preferably $R^3$ is hydroxyl.

One embodiment of the present invention concerns compounds of the Formula (I) or (II), or stereochemically isomeric forms thereof, for use in the treatment of chronic fatigue syndrome and/or in the treatment of infection by a gamma-retrovirus, wherein $L^1$ is $C_{1-6}$alkyleneoxy; preferably $L^1$ is $C_{1-4}$alkyleneoxy; preferably $L^1$ is ethyleneoxy.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $X^1$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^1$ is selected from N or $^+NR^8$, wherein $R^8$ is selected from $C_{6-12}$aryl or $C_{6-12}$aryl$C_{1-6}$alkyl; preferably $X^1$ is selected from N or $^+NR^8$, wherein $R^8$ is selected from $C_6$aryl or $C_6$aryl$C_{1-4}$alkyl; preferably $X^1$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^1$ is selected from N or $^+NR^8$, wherein $R^8$ is benzyl.

One embodiment of the present invention concerns compounds of the Formula (I), or stereochemically isomeric forms thereof, for use in the treatment of chronic fatigue syndrome and/or in the treatment of infection by a gamma-retrovirus, wherein each $X^2$ is independently selected from N or $^+NR^8$, wherein $R^8$ is selected from the group comprising $C_{1-6}$alkyl, $C_{6-12}$aryl and $C_{6-12}$aryl$C_{1-6}$alkyl; preferably each $X^2$ is independently selected from N or $^+NR^8$, wherein $R^8$ is selected from $C_{6-12}$aryl or $C_{6-12}$aryl$C_{1-6}$alkyl; preferably each $X^2$ is independently selected from N or $^+NR^8$, wherein $R^8$ is selected from $C_6$aryl or $C_6$aryl$C_{1-4}$alkyl; for example each $X^2$ is independently selected from N or $^+NR^8$, wherein $R^8$ is selected from the group comprising phenyl, biphenylyl, biphenylenyl, 1-naphthyl, 2-naphthyl, benzyl, dibenzylmethyl, methylphenylmethyl, 1-methyl-1-phenyl-ethyl, 1-phenyl-ethyl and 3-(2-naphthyl)-butyl; preferably each $X^2$ is independently selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably each $X^2$ is independently selected from N or $^+NR^8$, wherein $R^8$ is benzyl.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein $X^3$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^3$ is selected from N or $^+NR^8$, wherein $R^8$ is selected from $C_{6-12}$aryl or $C_{6-12}$aryl$C_{1-6}$alkyl; preferably $X^3$ is selected from N or $^+NR^8$, wherein $R^8$ is selected from $C_6$aryl or $C_6$aryl$C_{1-4}$alkyl; preferably $X^3$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^3$ is selected from N or $^+NR^8$, wherein $R^8$ is benzyl.

One embodiment of the present invention concerns compounds of the Formula (I), (II), (III), (IV) or (V), or stereochemically isomeric forms thereof, for use in the treatment of chronic fatigue syndrome and/or in the treatment of infection by a gamma-retrovirus, wherein at least one of $R^2$, $R^5$, $R^6$ or $R^8$ is selected from $C_{6-12}$aryl or $C_{6-12}$aryl$C_{1-6}$alkyl; preferably at least one of $R^2$, $R^5$, $R^6$ or $R^8$ is selected from $C_6$aryl or $C_6$aryl$C_{1-4}$alkyl; preferably at least one of $R^2$, $R^5$, $R^6$ or $R^8$ is selected from the group comprising phenyl, benzyl, phenethyl, methylphenylmethyl, 1-methyl-1-phenyl-ethyl and 1-phenyl-ethyl; preferably at least one of $R^2$, $R^5$, $R^6$ or $R^8$ is benzyl.

One embodiment of the present invention concerns compounds of the Formula (I), or stereochemically isomeric forms thereof, for use in the treatment of chronic fatigue syndrome and/or in the treatment of infection by a gamma-retrovirus, wherein $R^1$ and each $R^4$ are hydrogen.

One embodiment of the present invention concerns compounds of the Formula (I), or stereochemically isomeric forms thereof, for use in the treatment of chronic fatigue syndrome and/or in the treatment of infection by a gamma-retrovirus, wherein $R^2$, each $R^5$ and $R^6$ are hydrogen.

One embodiment of the present invention concerns compounds of the Formula (I), or stereochemically isomeric forms thereof, for use in the treatment of chronic fatigue syndrome and/or in the treatment of infection by a gamma-retrovirus, wherein
$X^1$, each $X^2$ and $X^3$ are N.

One embodiment of the present invention concerns compounds of the Formula (III) or (IV), or stereochemically isomeric forms thereof, for use in the treatment of chronic fatigue syndrome and/or in the treatment of infection by a gamma-retrovirus, wherein
p is 2.

One embodiment of the present invention concerns compounds of the Formula (II) or (III), or stereochemically isomeric forms thereof, for use in the treatment of chronic fatigue syndrome and/or in the treatment of infection by a gamma-retrovirus, wherein
$R^1$, $R^{41}$ and $R^{42}$ are hydrogen.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^2$, $R^{51}$ and $R^{52}$ are hydrogen.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$X^1$, $X^{21}$ and $X^{22}$ are N.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^{41}$ is selected from the group comprising hydrogen, hydroxyl, amino, $-OSi(CH_3)_2C(CH_3)_3$, $C_{1-6}$alkyl, $C_{1-6}$alkylcarbonyloxy and $C_{1-6}$alkoxy; preferably $R^{41}$ is selected from the group comprising hydrogen, hydroxyl, $C_{1-6}$alkyl, $C_{1-6}$alkylcarbonyloxy and $C_{1-6}$alkoxy; preferably $R^{41}$ is selected from the group comprising hydrogen, hydroxyl and $C_{1-6}$alkyl; preferably $R^{41}$ is selected from the group comprising hydrogen, hydroxyl and $C_{1-4}$alkyl; preferably $R^{41}$ is selected from hydrogen or hydroxyl; preferably $R^{41}$ is hydrogen.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^{42}$ is selected from the group comprising hydrogen, hydroxyl, amino, $-OSi(CH_3)_2C(CH_3)_3$, $C_{1-6}$alkyl, $C_{1-6}$alkylcarbonyloxy and $C_{1-6}$alkoxy; preferably $R^{42}$ is selected from the group comprising hydrogen, hydroxyl, $C_{1-6}$alkyl, $C_{1-6}$alkylcarbonyloxy and $C_{1-6}$alkoxy; preferably $R^{42}$ is selected from the group comprising hydrogen, hydroxyl and $C_{1-6}$alkyl; preferably $R^{42}$ is selected from the group comprising hydrogen, hydroxyl and $C_{1-4}$alkyl; preferably $R^{42}$ is selected from hydrogen or hydroxyl; preferably $R^{42}$ is hydrogen.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^{51}$ is selected from the group comprising hydrogen, $C_{1-6}$alkyl, $C_{6-12}$aryl and $C_{6-12}$aryl$C_{1-6}$alkyl; preferably $R^{51}$ is selected from the group comprising hydrogen, $C_{6-12}$aryl and $C_{6-12}$aryl$C_{1-6}$alkyl; preferably $R^{51}$ is selected from the group comprising hydrogen, $C_6$aryl and $C_6$aryl$C_{1-4}$alkyl; preferably $R^{51}$ is selected from the group comprising hydrogen, phenyl, benzyl, phenethyl, methylphenylmethyl, 1-methyl-1-phenyl-ethyl and 1-phenyl-ethyl; preferably $R^{51}$ is selected from hydrogen or benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^{52}$ is selected from the group comprising hydrogen, $C_{1-6}$alkyl, $C_{6-12}$aryl and $C_{6-12}$aryl$C_{1-6}$alkyl; preferably $R^{52}$ is selected from the group comprising hydrogen, $C_{6-12}$aryl and $C_{6-12}$aryl$C_{1-6}$alkyl; preferably $R^{52}$ is selected from the group comprising hydrogen, $C_6$aryl and $C_6$aryl$C_{1-4}$alkyl; preferably $R^{52}$ is selected from the group comprising hydrogen, phenyl, benzyl, phenethyl, methylphenylmethyl, 1-methyl-1-phenyl-ethyl and 1-phenyl-ethyl; preferably $R^{52}$ is selected from hydrogen or benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$X^{21}$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^{21}$ is selected from N or $^+NR^8$, wherein $R^8$ is selected from $C_{6-12}$aryl or $C_{6-12}$aryl$C_{1-6}$alkyl; preferably $X^{21}$ is selected from N or $^+NR^8$, wherein $R^8$ is selected from $C_6$aryl or $C_6$aryl$C_{1-4}$alkyl; preferably $X^{21}$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^{21}$ is selected from N or $^+NR^8$, wherein $R^8$ is benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$X^{22}$ is selected from N or $^+NR^8$, wherein $R^8$ is selected from the group comprising $C_{1-6}$alkyl, $C_{6-12}$aryl and $C_{6-12}$aryl$C_{1-6}$alkyl; preferably $X^{22}$ is selected from N or $^+NR^8$, wherein $R^8$ is selected from $C_{6-12}$aryl or $C_{6-12}$aryl$C_{1-6}$alkyl; preferably $X^{22}$ is selected from N or $^+NR^8$, wherein $R^8$ is selected from $C_6$aryl or $C_6$aryl$C_{1-4}$alkyl; preferably $X^{22}$ is selected from N or $^+NR^8$, wherein $R^8$ is selected from the group comprising phenyl, benzyl, phenethyl, methylphenylmethyl, 1-methyl-1-phenyl-ethyl and 1-phenyl-ethyl; preferably $X^{22}$ is selected from N or $^+NR^8$, wherein $R^8$ is benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
at least one of $R^2$, $R^{51}$, $R^{52}$ or $R^8$ is selected from $C_{6-12}$aryl or $C_{6-12}$aryl$C_{1-6}$alkyl; preferably at least one of $R^2$, $R^{51}$, $R^{52}$ or $R^8$ is selected from $C_6$aryl or $C_6$aryl$C_{1-4}$alkyl; preferably at least one of $R^2$, $R^{51}$, $R^{52}$ or $R^8$ is selected from the group comprising phenyl, benzyl, phenethyl, methylphenylmethyl, 1-methyl-1-phenyl-ethyl and 1-phenyl-ethyl; preferably at least one of $R^2$, $R^{51}$, $R^{52}$ or $R^8$ is benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
only one of $R^2$, $R^{51}$, $R^{52}$ or $R^8$ is selected from $C_{6-12}$aryl or $C_{6-12}$aryl$C_{1-6}$alkyl; preferably only one of $R^2$, $R^{51}$, $R^{52}$ or $R^8$ is selected from $C_6$aryl or $C_6$aryl$C_{1-4}$alkyl; preferably only one of $R^2$, $R^{51}$, $R^{52}$ or $R^8$ is selected from the group comprising phenyl, benzyl, phenethyl, methylphenylmethyl, 1-methyl-1-phenyl-ethyl and 1-phenyl-ethyl; preferably only one of $R^2$, $R^{51}$, $R^{52}$ or $R^8$ is benzyl.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein $R^2$, $R^{51}$ and $R^{52}$ are independently selected from hydrogen or benzyl and only one of $R^2$, $R^{51}$ or $R^{52}$ is benzyl, and $X^1$, $X^{21}$ and $X^{22}$ are N.

One embodiment of the present invention concerns compounds of the Formula (II), (III), (IV) or (V), or stereochemically isomeric forms thereof, for use in the treatment of chronic fatigue syndrome and/or in the treatment of infection by a gamma-retrovirus, wherein
$R^2$, $R^{51}$ and $R^{52}$ are hydrogen, and $X^1$, $X^{21}$ and $X^{22}$ are independently selected from N or $^+NR^8$, wherein $R^8$ is benzyl and only one of $X^1$, $X^{21}$ or $X^{22}$ is $NR^8$.

In further embodiments, the invention relates to compounds as described above, wherein said compounds are used in combination with at least one other pharmacologically active compound, preferably a viral inhibitor. More particularly, the present invention relates to the therapeutic use of the compounds used in combination with at least one inhibitor of a virus wherein said virus is causing CFS or, wherein said virus is a gamma-retrovirus, in particular XMRV or MLV. In an embodiment, the at least one other pharmacologically active compound is selected form the group comprising azidothymidine (AZT), raltegravir, tenofovir, tenofovir disoproxil fumarate (TDF), didanosine, lamivudine, staduvine, abacavir, foscarnet, amantadine, kutapressin, hepapressin, isoprinosine, Gc protein-derived macrophage activating factor (GcMAF), ampligen/poly I:poly C12U, minocycline, doxycycline, azithromycin and the cytidine deaminases APOBEC3F and APOBEC3G.

In further embodiments, the invention relates to compounds as described above, wherein said compounds are used in a pharmaceutical composition comprising a pharmaceutically acceptable excipient and a therapeutically effective amount of at least one compound of Formula (I), (II), (III), (IV), (V), (VI), (VII) or (VIII) as described above, for use in the treatment of chronic fatigue syndrome and/or in the treatment of infection by a gamma-retrovirus.

The term "therapeutically effective amount" as used herein means that amount of compound or conjugate or pharmaceutical agent that elicits the biological or medicinal response in a tissue, system, animal or human that is being sought by a researcher, veterinarian, medical doctor or other clinician, which includes alleviation of the symptoms of the disease being treated.

In further embodiments, the invention provides compounds of Formula (I), (II), (III), (IV), (V), (VI), (VII) or (VIII), or stereochemically isomeric forms thereof, for use in the treatment of individuals diagnosed with CFS and/or for use in the treatment of individuals diagnosed with infection by a gamma-retrovirus.

According to further embodiments, the invention provides a use of a compound of Formula (I), (II), (III), (IV), (V), (VI), (VII) or (VIII), or stereochemically isomeric forms thereof, in the manufacture of a medicament for the treatment of CFS and/or for the treatment of infection by a gamma-retrovirus.

In further embodiments, the invention provides a use of a compound as described above in the manufacture of a medicament for the treatment of CFS and/or for inhibiting infection by a gamma-retrovirus, wherein said compound is used in a pharmaceutical composition comprising a pharmaceutically acceptable excipient and a therapeutically effective amount of at least one compound of Formula (I), (II), (III), (IV), (V), (VI), (VII) or (VIII).

The present invention also relates to a method for the treatment of chronic fatigue syndrome and/or for the treatment of infection by a gamma-retrovirus, comprising the step of administering a therapeutically effective amount of a compound of Formula (I), (II), (III), (IV), (V), (VI), (VII) or (VIII), or stereochemically isomeric forms thereof, to an individual in need thereof.

The present invention also relates to a method for the treatment of chronic fatigue syndrome and/or for the treatment of infection by XMRV and/or MLV, comprising the step of administering a therapeutically effective amount of a compound of Formula (I), (II), (III), (IV), (V), (VI), (VII) or (VIII), or stereochemically isomeric forms thereof, to an individual in need thereof.

The term "individual", as used herein, refers to an animals, for example to any species or subspecies of bird, mammal, fish, amphibian, or reptile, preferably a mammal, more preferably a human being.

The compounds of the present invention can be administered to animals, preferably to a mammal, more preferably to humans for the treatment or prevention of any one of the diseases mentioned herein. In view of the utility of the compounds of Formula (I), (II), (III), (IV), (V), (VI), (VII) or (VIII), there is provided a method of treating animals, including mammals, preferably humans, suffering from or a method of preventing animals, including mammals, preferably humans, to suffer from any one of the diseases mentioned herein.

For pharmaceutical use, the compounds may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form of a pro-drug such as an ester. The term "solvate", as used herein, comprises the hydrates and solvent addition forms which the compounds of the present invention are able to form, as well as the salts thereof. Examples of such forms are e.g. hydrates, alcoholates and the like. Such salts, hydrates, solvates, etc., and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087, and U.S. Pat. No. 6,372,733.

For therapeutic use, the salts of the compounds according to the invention are those wherein the counterion is pharmaceutically or physiologically acceptable.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

The pharmaceutically acceptable esters of the compounds according to the invention refer to non-toxic esters, preferably the alkyl esters such as methyl, ethyl, propyl, isopropyl, butyl, isobutyl, or pentyl esters, of which the methyl ester is preferred. However, other esters such as phenyl-alkyl may be employed if desired.

Compounds for use in the invention have the advantage of exhibiting a low toxicity level. "Toxicity" is related to the detrimental effect a compound may exhibit on healthy cells, tissues or organs. The toxicity level of the compounds is surprisingly low. The present compounds combine the essential features of a good antiviral activity and a low level of toxicity. In view of their low toxicity, the compounds according to the invention may be used during longer periods of treatments. This is advantageous because of the chronic nature of chronic fatigue syndrome and infections caused by gamma-retroviruses.

In addition, although generally, with respect to the salts of the compounds, pharmaceutically acceptable salts are preferred, it should be noted that the invention in its broadest sense also included non-pharmaceutically acceptable salts, which may for example be used in the isolation and/or purification of the compounds. For example, salts formed with optically active acids or bases may be used to form diastereoisomeric salts that can facilitate the separation of optically active isomers of the compounds of Formula (I) or any subgroup thereof.

The invention also generally covers all pharmaceutically acceptable pro-drugs of the compounds of Formula (I), (II), (III), (IV), (V), (VI), (VII) or (VIII), and any subgroup thereof, for which general reference is made to the prior art cited herein below.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int. Ed. 1992, "Biotransformation of Drugs", p 13-15) describing pro-drugs generally is hereby incorporated. Pro-drugs of the compounds can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792. Pro-drugs are characterized by increased bioavailability and are readily metabolized into the active inhibitors in vivo.

The pharmaceutical composition can be prepared in a manner known per se to one of skill in the art. For this purpose, at least one compound according to the invention having Formula (I), (II), (III), (IV), (V), (VI), (VII) or (VIII), or any subgroup or derivative thereof, one or more solid or liquid pharmaceutical excipients and, if desired, in combination with other pharmaceutical active compounds, are brought into a suitable administration form or dosage form which can then be used as a pharmaceutical in human medicine or veterinary medicine.

Particular forms of the pharmaceutical composition may be, for example, solutions, suspensions, emulsions, creams, tablets, pills, capsules, nasal sprays, liposomes or microreservoirs, especially compositions in orally ingestible or sterile injectable form, for example, as sterile injectable aqueous or oleaginous suspensions or suppositories and sterile packaged powders (which are usually reconstituted prior to use) for administration as a bolus and/or for continuous administration. The solid carrier may comprise one or more excipients, e.g. lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, fillers, disintegrating agents, binders, e.g. cellulose, carboxymethylcellulose or starch or anti-stick agents, e.g. magnesium stearate, to prevent tablets from adhering to tabletting equipment, (sterile) water, methylcellulose, methyl- and propylhydroxybenzoates, talc, magnesium stearate, edible oils, vegetable oils and mineral oils or suitable mixtures thereof. Tablets, pills and boluses may be formed so as to disintegrate rapidly or to provide slow release of the active ingredient. The formulations can optionally contain other pharmaceutically active substances (which may or may not lead to a synergistic effect with the compounds) and other substances that are commonly used in pharmaceutical formulations, such as lubricating agents, wetting agents, emulsifying, and suspending agents, dispersing agents, disintegrants, bulking agents, fillers, preserving agents, sweetening agents, flavoring agents, flow regulators, release agents, etc. The compositions may also be formulated so as to provide rapid, sustained, or delayed release of the active compound(s) contained therein, for example using liposomes or hydrophilic polymeric matrices based on natural gels or synthetic polymers.

In order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the present compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD; hydroxyalkyl, particularly hydroxyethyl, hydroxypropyl or hydroxybutyl; carboxyalkyl, particularly carboxymethyl or carboxyethyl; alkylcarbonyl, particularly acetyl; alkyloxycarbonylalkyl or carboxyalkyloxyalkyl, particularly carboxymethoxypropyl or carboxyethoxypropyl; alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxy groups are etherified with different groups such as, for example, hydroxypropyl and hydroxyethyl. An interesting way of formulating the compounds according to the invention in combination with a cyclodextrin or a derivative thereof has been described in EP-A-721,331. Although the formulations described therein are with antifungal active ingredients, they are equally interesting for formulating the compounds according to the invention. Said formulations may also be rendered more palatable by adding pharmaceutically acceptable sweeteners and/or flavors.

More in particular, the compositions may be formulated in a pharmaceutical formulation comprising a therapeutically effective amount of particles consisting of a solid dispersion of the present compounds and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 20° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule. The compounds according to the invention as defined hereinabove can be prepared by first preparing a solid dispersion of the compounds according to the invention, and then optionally grinding or milling that dispersion. Various techniques exist for preparing solid dispersions including melt-extrusion, spray-drying and solution-evaporation, melt-extrusion being preferred.

It may further be convenient to formulate the compounds according to the invention in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing the at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

For these purposes, the compounds or the pharmaceutical composition for use in the present invention may be administered orally, parenterally, i.e. including subcutaneous injections, intravenous, intramuscular, intrasternal injection or infusion techniques, by inhalation spray, or rectally, in dosage unit formulations containing conventional non-toxic pharmaceutically acceptable carriers, adjuvants and vehicles. The at least one compound will generally be administered in an "effective amount", by which is meant any amount of a compound of the Formula I that, upon suitable administration, is sufficient to achieve the desired therapeutic or prophylactic effect in the individual to which it is administered. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087, and U.S. Pat. No. 6,372,733, and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

The oral administration of a pharmaceutical composition comprising at least one compound according to the invention, or a pharmaceutically acceptable salt or ester or solvate thereof, is suitably accomplished by uniformly and intimately blending together a suitable amount of said compound in the form of a powder, optionally also including a finely divided solid carrier, and encapsulating the blend in, for example, a hard gelatin capsule. The solid carrier can include one or more substances, which act as binders, lubricants, disintegrating agents, coloring agents, and the like. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Oral administration of a pharmaceutical composition comprising at least one compound according to the invention, or a pharmaceutically acceptable salt or ester and/or solvate thereof can also be accomplished by preparing capsules or tablets containing the desired amount of said compound, optionally blended with a solid carrier as described above. Compressed tablets containing the pharmaceutical composition of the invention can be prepared by uniformly and intimately mixing the active ingredient with a solid carrier such as described above to provide a mixture having the necessary compression properties, and then compressing the mixture in a suitable machine to the shape and size desired. Molded tablets maybe made by molding in a suitable machine, a mixture of powdered compound according to the invention moistened with an inert liquid diluent.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the present compounds or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compounds or pharmaceutical composition if desired with the substances customary therefor such as solubilizers, emulsifiers or further auxiliaries are brought into solution, suspension, or emulsion. The compounds can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In addition to administration with conventional carriers, the compounds of the present invention may be administered by a variety of specialized oligonucleotide or nucleic acid delivery techniques such as by encapsulation in various encapsulating materials, such as in unilamellar liposomes (Bayard et al., *Eur. J. Biochem.* 151: 319, 1985) or by conjugation to carrier molecules such as poly(L-lysine). Reconstituted Sendai virus envelopes have been successfully used to deliver RNA and DNA to cells (Arad et al., *Biochem. Biophys. Acta.* 85: 88, 1986). Moreover, the virus envelope is not limited to Sendai virus, but could include encapsulation in any retroviral amphotrophic particle. These techniques may be utilized for introduction of the present 2',5'-oligoadenylate derivative compounds into cells.

The pharmaceutical compositions of this invention can be administered to humans in dosage ranges specific for each compound comprised in said compositions. The compounds comprised in said composition can be administered together or separately.

It will be understood, however, that specific dose level and frequency of dosage for any particular patient may be varied and will depend upon a variety of factors including the activity of the specific compound of the invention employed, the metabolic stability and length of action of that compound, the age, body weight, general health, sex, diet, mode and time of administration, rate of excretion, drug combination, the severity of the particular condition, and the host undergoing therapy.

The following examples are meant to illustrate the present invention. These examples are presented to exemplify the invention and are not to be considered as limiting the scope of the invention.

EXAMPLES

Example 1

$N^1$-benzyl-3'-deoxyadenylyl-(2'-5')-3'-deoxyadenylyl-(2'-5')-3'-deoxyadenylyl-(2'-2")—$N^9$-[(2"-hydroxy-ethoxy)-methyl]-adenine Inhibits Replication of the Gamma-Retrovirus, XMRV in $CD4^+$ Cells Purified from XMRV-Positive Patients First, the activity of 2-$5A^{N1B}$ on XMRV-replication is tested in $CD4^+$ T lymphocytes purified from healthy individuals. To determine the effective dose of 2-$5A^{N1B}$ during acute XMRV infection, freshly isolated $CD4^+$ T cells are treated with three concentrations of 2-$5A^{N1B}$ (10, 100 and 1000 nM) and then infected with XMRV. XMRV-replication is assessed in culture supernatants by ELISA. A significant decrease in XMRV-replication is observed in 2-$5A^{N1B}$ treated $CD4^+$ T cells, compared to untreated controls, 96 h post-infection.

Secondly, the activity of 2-$5A^{N1B}$ is tested on chronically infected cells derived from XMRV-positive individuals. XMRV-positive adults are recruited from the clinic. The antiviral response to 2-$5A^{N1B}$ in vitro is assessed by ELISA in the supernatants of cultured CD4+ cells. 2-$5A^{N1B}$ significantly inhibits replication of wild-type XMRV in purified CD4+ T lymphocytes when compared to untreated cells.

What is claimed is:

1. A method for the treatment of chronic fatigue syndrome and/or for the treatment of infection by a gamma-retrovirus in an individual in need thereof comprising the step of administering a therapeutically effective amount of a compound of Formula (I), or stereochemically isomeric forms thereof, to said individual,

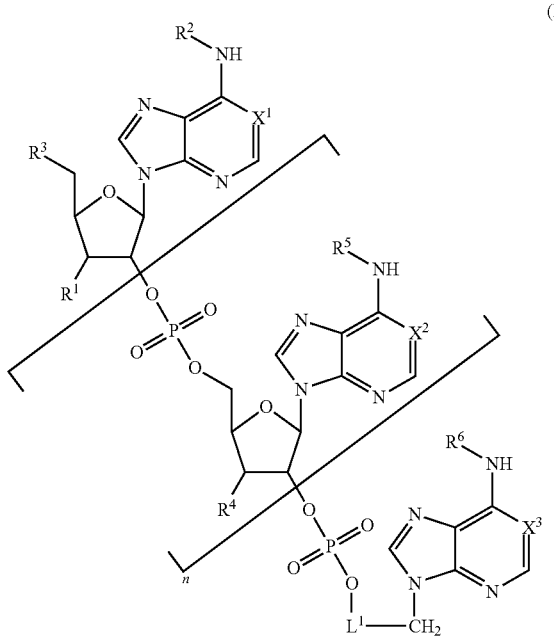

(I)

wherein n is an integer selected from 1 to 8;

$R^1$ is selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy;

$R^2$ is selected from the group comprising hydrogen, $C_{1-6}$alkyl, $C_{6-12}$aryl and $C_{6-12}$aryl$C_{1-6}$alkyl;

each $R^4$ is independently selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy;

each $R^5$ is independently selected from the group comprising hydrogen, $C_{1-6}$alkyl, $C_{6-12}$aryl and $C_{6-12}$aryl$C_{1-6}$alkyl;

$R^6$ is selected from the group comprising hydrogen, $C_{1-6}$alkyl, $C_{6-12}$aryl and $C_{6-12}$aryl$C_{1-6}$alkyl;

$R^3$ is selected from the group comprising hydroxyl,

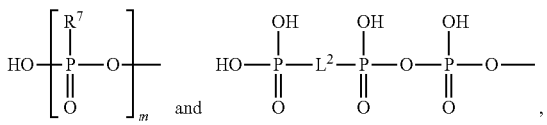

and m is an integer selected from 1, 2 or 3, each $R^7$ is independently selected from the group comprising OH, SH, $C_{1-6}$alkyl and $C_{1-6}$alkoxy, and $L^2$ is selected from —NH— or methylene;

$L^1$ is selected from $C_{1-6}$alkylene or $C_{1-6}$alkyleneoxy;

$X^1$ is selected from N or $^+NR^8$, wherein $R^8$ is selected from the group comprising $C_{1-6}$alkyl, $C_{6-12}$aryl and $C_{6-12}$aryl$C_{1-6}$alkyl;

each $X^2$ is independently selected from N or $^+NR^8$, wherein $R^8$ is selected from the group comprising $C_{1-6}$alkyl, $C_{6-12}$aryl and $C_{6-12}$aryl$C_{1-6}$alkyl;

$X^3$ is selected from N or $^+NR^8$, wherein $R^8$ is selected from the group comprising $C_{1-6}$alkyl, $C_{6-12}$aryl and $C_{6-12}$aryl$C_{1-6}$alkyl; and wherein at least one of $R^2$, $R^5$, $R^6$ or $R^8$ is selected from $C_{6-12}$aryl or $C_{6-12}$aryl$C_{1-6}$alkyl;

or, a pharmaceutically acceptable salt thereof.

2. The method according to claim 1, wherein said compound is a compound of Formula (II), or stereochemically isomeric forms thereof,

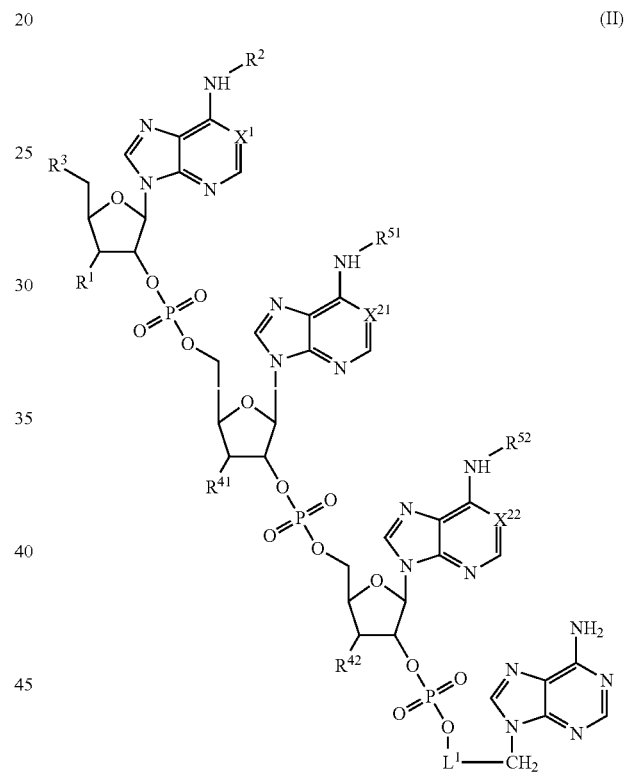

(II)

wherein $R^1$, $R^2$, $R^3$, $X^1$ and $L^1$ have the same meaning as that defined in claim 1;

$R^{41}$ is selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy;

$R^{42}$ is selected from the group comprising hydrogen, hydroxyl, amino, —OSi(CH$_3$)$_2$C(CH$_3$)$_3$, $C_{1-6}$alkyl, $C_{1-6}$alkylcarbonyloxy and $C_{1-6}$alkoxy;

$R^{51}$ is selected from the group comprising hydrogen, $C_{1-6}$alkyl, $C_{6-12}$aryl and $C_{6-12}$aryl$C_{1-6}$alkyl;

$R^{52}$ is selected from the group comprising hydrogen, $C_{1-6}$alkyl, $C_{6-12}$aryl and $C_{6-12}$aryl$C_{1-6}$alkyl;

$X^{21}$ is selected from N or $^+NR^8$, wherein $R^8$ is selected from the group comprising $C_{1-6}$alkyl, $C_{6-12}$aryl and $C_{6-12}$aryl$C_{1-6}$alkyl;

X²² is selected from N or ⁺NR⁸, wherein R⁸ is selected from the group comprising $C_{1-6}$alkyl, $C_{6-12}$aryl and $C_{6-12}$aryl$C_{1-6}$alkyl; and wherein at least one of R², R⁵¹, R⁵² or R⁸ is selected from $C_{6-12}$aryl or $C_{6-12}$aryl$C_{1-6}$alkyl;

or, a pharmaceutically acceptable salt thereof.

3. The method according to claim 2, wherein said compound is a compound of Formula (III), or stereochemically isomeric forms thereof,

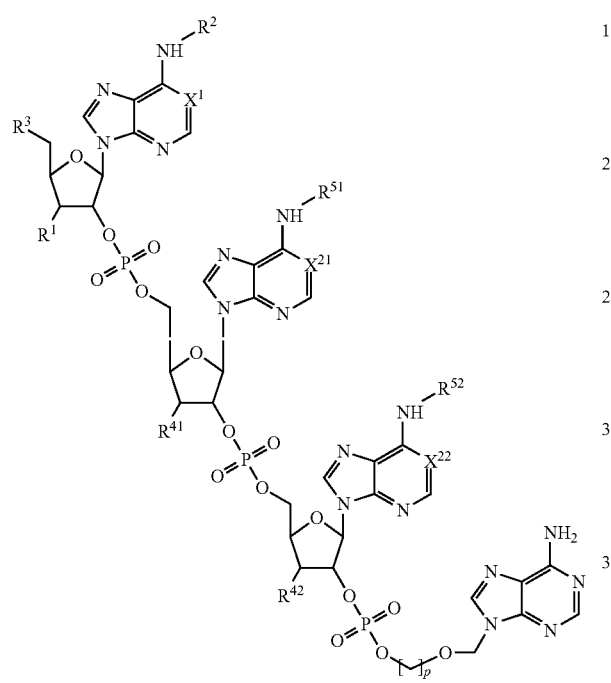

(III)

wherein p is an integer selected from 1, 2, 3, 4, 5 or 6;

R¹, R², R³, R⁴¹, R⁴², R⁵¹, R⁵², X¹, X²¹ and X²² have the same meaning as that defined in claim 2.

4. The method according to claim 2, wherein said compound is a compound of Formula (IV), or stereochemically isomeric forms thereof,

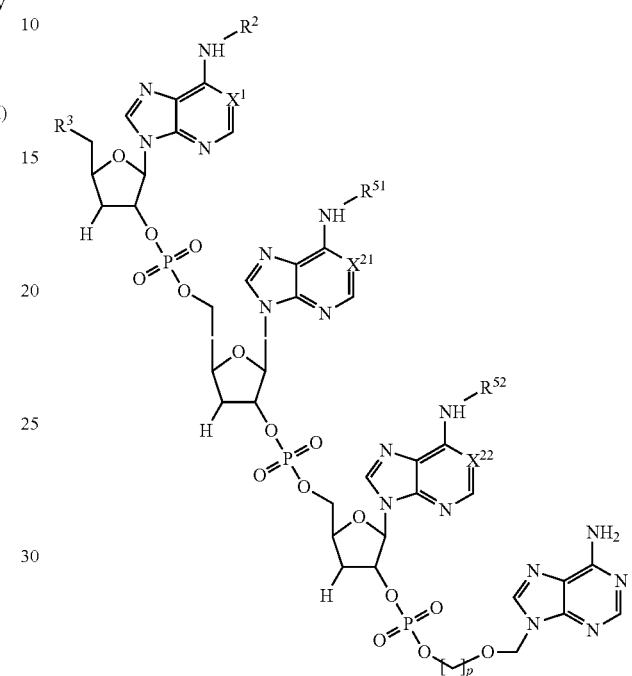

(IV)

wherein p is an integer selected from 1, 2, 3 or 4;

R², R³, R⁵¹, R⁵², X¹, X²¹ and X²² have the same meaning as that defined in claim 2.

5. The method according to claim 2, wherein said compound is a compound of Formula (V), or stereochemically isomeric forms thereof,

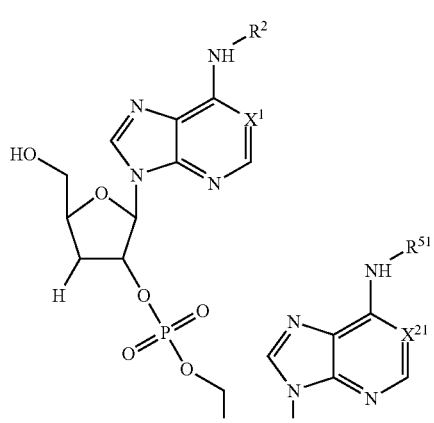

(V)

-continued

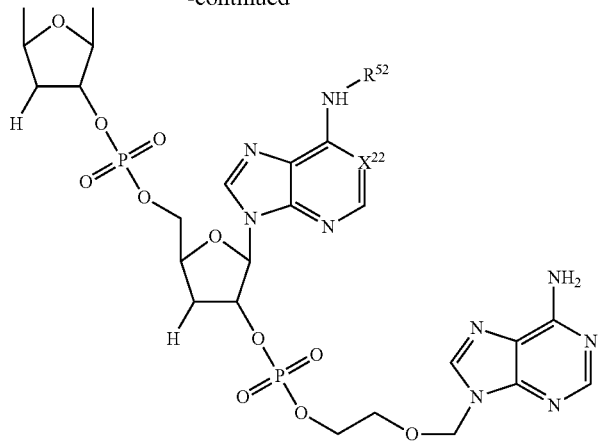

wherein
$R^2, R^{51}, R^{52}, X^1, X^{21}$ and $X^{22}$ have the same meaning as that defined in claim 2.

6. The method according to claim 2, wherein only one of $R^2, R^{51}, R^{52}$ or $R^8$ is selected from $C_{6-12}$aryl or $C_{6-12}$aryl$C_{1-6}$ alkyl.

7. The method according to claim 2, wherein
$R^2, R^{51}$ and $R^{52}$ are independently selected from hydrogen or benzyl and only one of $R^2, R^{51}$ or $R^{52}$ is benzyl, and $X^1, X^{21}$ and $X^{22}$ are N.

8. The method according to claim 2, wherein
$R^2, R^{51}$ and $R^{52}$ are hydrogen, and
$X^1, X^{21}$ and $X^{22}$ are independently selected from N or $^+NR^8$, wherein $R^8$ is benzyl and only one or $X^1, X^{21}$ or $X^{22}$ is $NR^8$.

9. The method according to claim 1, wherein said compound is a compound of Formula (VI), or stereochemically isomeric forms thereof (VI)

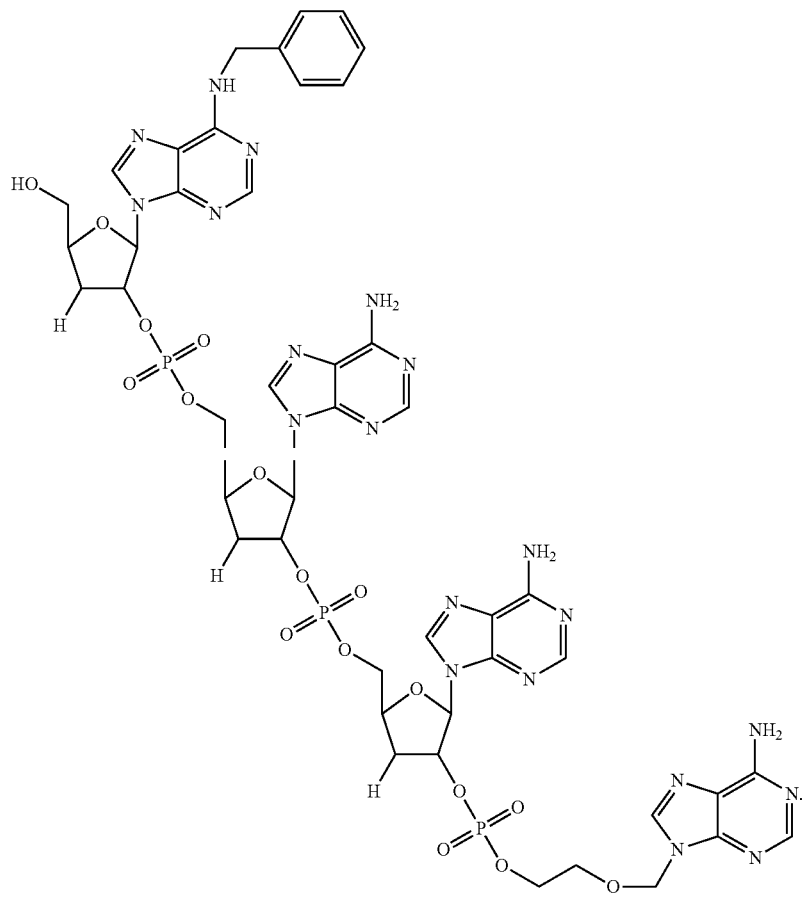

10. The method according to claim 1, wherein said compound is a compound of Formula (VII), or stereochemically isomeric forms thereof
(VII)
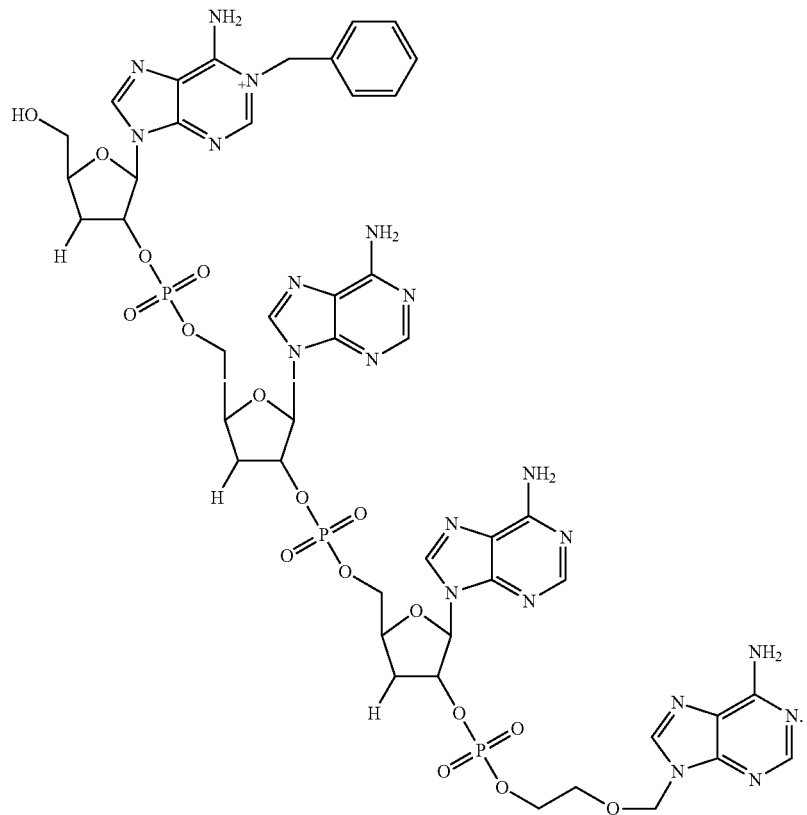
11. The method according to claim 1, wherein said compound is a compound of Formula (VIII), or stereochemically isomeric forms thereof
(VIII)
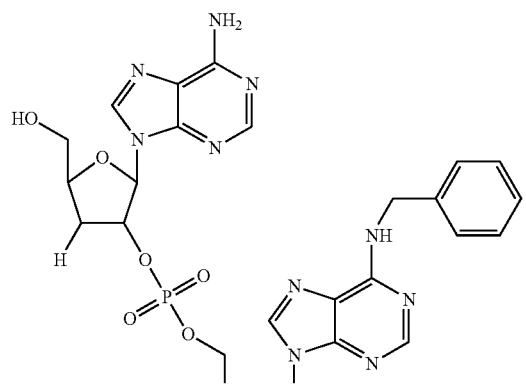

-continued

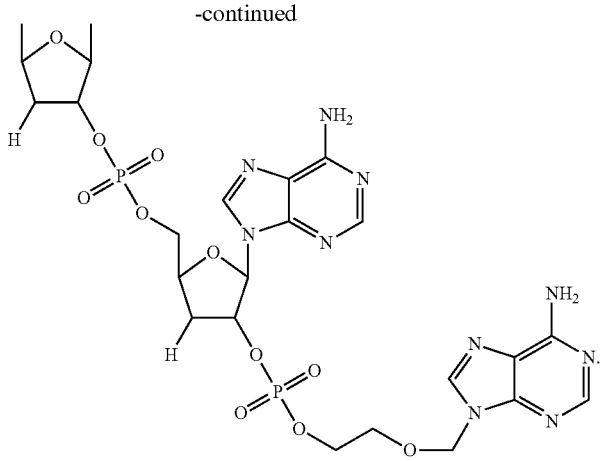

12. The method according to claim 1, wherein said compound is used in combination with at least one other pharmacologically active compound.

13. The method according to claim 12, wherein said at least one other pharmaceutically active compound is a viral inhibitor.

14. The method according to claim 13, wherein said at least one other pharmacologically active compound is selected form the group comprising azidothymidine (AZT), raltegravir, tenofovir, tenofovir disoproxil fumarate (TDF), didanosine, lamivudine, staduvine, abacavir, foscarnet, amantadine, kutapressin, hepapressin, isoprinosine, Gc protein-derived macrophage activating factor (GcMAF), ampligen/poly I:poly C12U, minocycline, doxycycline, azithromycin and the cytidine deaminases APOBEC3F and APOBEC3G.

15. The method according to claim 1, wherein said compound is used in a pharmaceutical composition comprising a pharmaceutically acceptable excipient and a therapeutically effective amount of at least one compound of Formula (I).

* * * * *